United States Patent
Boston

(10) Patent No.: US 6,437,188 B1
(45) Date of Patent: Aug. 20, 2002

(54) TREATMENT OF DITERTIARYDODECYLDISULFIDE WITH AMMONIUM HYDROXIDE FOR COLOR REMOVAL

(75) Inventor: Ernest B. Boston, Borger, TX (US)

(73) Assignee: Chevron Phillips Chemical Company, LP, Houston, TX (US)

( * ) Notice: Subject to any disclaimer, the term of this patent is extended or adjusted under 35 U.S.C. 154(b) by 0 days.

(21) Appl. No.: 09/932,697

(22) Filed: Aug. 17, 2001

(51) Int. Cl.[7] ............................................. C07C 319/28
(52) U.S. Cl. .......................................................... 568/21
(58) Field of Search ............................................. 568/21

(56) References Cited

U.S. PATENT DOCUMENTS

| 4,072,718 A | * | 2/1978 | Billings | |
| 4,355,183 A | * | 10/1982 | Nash et al. | 568/19 |
| 5,218,147 A | * | 6/1993 | Shaw | 568/21 |
| 5,659,086 A | * | 8/1997 | Pauwels et al. | 568/27 |

* cited by examiner

Primary Examiner—Jean F. Vollano
(74) Attorney, Agent, or Firm—Steven Owen

(57) ABSTRACT

A process is provided for removing color byproducts and residues from a colored ditertiarydodecyldisulfide (DTDDDS) stream. Particularly, a process is provided for removing the color byproducts and residues from the colored DTDDDS stream with ammonium hydroxide (NH$_4$OH) to produce a DTDDDS product.

10 Claims, No Drawings

TREATMENT OF DITERTIARYDODECYLDISULFIDE WITH AMMONIUM HYDROXIDE FOR COLOR REMOVAL

FIELD OF THE INVENTION

This invention relates to a process for removing color byproducts and residues from a colored ditertiarydodecyldisulfide (DTDDDS) stream by contacting the colored DTDDDS stream with ammonium hydroxide ($NH_4OH$) to produce a DTDDDS product.

BACKGROUND OF THE INVENTION

DTDDDS is produced by oxidation of tertiarydodecylmercaptan using air. During the production of DTDDDS, colored byproducts and residues may be produced yielding a colored DTDDDS stream. These colored byproducts and residues are difficult to remove in a plant environment. In addition, when the colored DTDDDS stream is filtered, it may fail to meet product color specification. Typically, the color specification for a DTDDDS product is about 1 to about 2 using a Gardner color test. The colored DTDDDS stream generally has a color of about 3 to about 6 using a Gardner color test.

An inventive solution has been discovered to remove the color byproducts and residues from the colored DTDDDS stream to produce a DTDDDS product.

SUMMARY OF THE INVENTION

It is an object of this invention to provide a process for removing color byproducts and residues from a colored DTDDDS stream to produce a DTDDDS product.

It is another object of this invention to provide a process for removing color byproducts and residues from a colored DTDDDS stream to produce a DTDDDS product wherein the color range of the DTDDDS product is about 1 to about 2 on a Gardner color test.

In accordance with this invention, a process for removing colored byproducts and residues from a colored DTDDDS stream is provided. The process comprises:

(a) Contacting $NH_4OH$ and the colored DTDDDS stream to produce a mixture;

(b) Water washing the mixture to produce a washed mixture;

(c) Separating the washed mixture to produce a byproduct stream and a wet DTDDDS product; and (d) Drying the wet DTDDDS product to produce a DTDDDS product.

DETAILED DESCRIPTION OF THE INVENTION

A process to remove color byproducts and residues from a colored DTDDDS stream to produce a DTDDDS product is provided, said process comprising:

(a) Contacting $NH_4OH$ and the colored DTDDDS stream to produce a mixture;

(b) Water washing the mixture to produce a washed mixture;

(c) Separating the washed mixture to produce a byproduct stream and a wet DTDDDS product, and (d) Drying the wet DTDDDS product to produce the DTDDDS product.

The colored DTDDDS stream can be produced by any method known in the art. Typically the colored DTDDDS stream is produced by oxidation of tertiarydodecylmercaptan using air. Copper catalysts often are used in the production of DTDDDS. Generally, the colored DTDDDS stream produced has a color in a range of about 3 to about 6 utilizing a Gardner color test (ASTM D-1544). The color specification for the DTDDDS product is in a range of about 1 to about 2 on a Gardner color test and most preferably, the color specification is 1 on a Gardner color test.

The first step of the process is contacting $NH_4OH$ with the colored DTDDDS stream to produce a mixture. The contacting can be conducted by any method known in the art. Generally, a $NH_4OH$ solution containing about 25% to about 35% by weight $NH_3$ is utilized. Preferably, the $NH_4OH$ solution contains about 28% to about 32% by weight $NH_3$. Typically, the $NH_4OH$ and colored DTDDDS stream are contacted in a ratio of about 1 to about 2 parts $NH_4OH$ to about 100 parts of the colored DTDDDS stream.

Generally, the contacting of the $NH_4OH$ with the colored DTDDDS stream is conducted at a temperature range of about 80° F. to about 125° F., preferably at a temperature range of 85° F. to 120° F. The contacting of the $NH_4OH$ with the colored DTDDDS stream is for a duration of about 12 hours to about 72 hours. The duration of the contacting depends on the reactivity of the colored DTDDDS stream. Preferably, the duration of the contacting is from about 24 hours to about 48 hours. The contacting yields a mixture comprising DTDDDS, $NH_4OH$, and color byproducts and residues.

The second step of the process is water washing the mixture to produce a washed mixture. Generally, a quantity of water ranging from about 10% to about 30% by weight of the colored DTDDDS stream is used. The $NH_4OH$ is soluble in water so the water wash can proceed rapidly. Typically, the water wash step is conducted at a temperature in a range of about 70° F. to about 100° F. The washed mixture comprises DTDDDS, $NH_4OH$, water, and color byproducts and residues. The third step of the process is separating the washed mixture to produce a byproduct stream and a wet DTDDDS product. The separating occurs in a temperature range of about 70° F. to about 100° F. and over a period of time in a range of about 2 hours to about 72 hours. Preferably, the separating occurs over a period of time in a range from about 48 hours to about 72 hours. The separating can be completed in any type of process equipment. For example, the separating can be accomplished in a tank to remove the wet DTDDDS product. Then, wet DTDDDS product can be further separated by filtering, in order to remove water.

The fourth step of the process is drying the wet DTDDDS stream to produce a DTDDDS product with a color range of about 1 to about 2 on the Gardner color test and a moisture content of less than about 10 ppm by weight water. Preferably, the DTDDDS product has a Gardner color test number of 1 and a moisture content of less than 10 ppm by weight water. Drying can be conducted by any process known in the art. Generally, the wet DTDDDS stream is dried at a temperature in a range of about 70° F. to about 100° F. The drying is conducted for a duration sufficient to achieve a moisture content of less than 10 ppm by weight water. For example, drying can be accomplished by utilizing desiccant or a filtering system.

EXAMPLES

The following examples are provided to assist a person skilled in the art with further illustrations of this invention. These examples are intended to be illustrative of the invention but are not meant to be construed as limiting the reasonable scope of the invention.

Example #1

In a laboratory test, 133.6 grams colored DTDDDS stream was mixed with 2.6 grams of a $NH_4OH$ solution (28–30% by wt $NH_3$) in a quart jar at a temperature in a range of 85° F. to 120° F. to produce a mixture. Since $NH_4OH$ does not readily dissolve in DTDDDS, the mixture was stirred using a magnetic stirrer for about 30 hours in the lab for acceptable color reduction. The mixture was then washed with 28 grams of water at a temperature range of 70° F. to 100° F. using a separatory funnel to produce a washed mixture consisting of DTDDDS, colored byproducts, water and $NH_4OH$. The stirring was stopped and the washed mixture was allowed to separate over a period of 2 hours to produce a wet DTDDDS product and byproduct stream. The wet DTDDDS was first passed though a filtration paper and then dried with air to produce a DTDDDS product with a color range of about 1 to about 2 on the Gardner color test and a moisture content of less than 10 ppm water by weight.

Example #2

In a commercial test, a colored DTDDDS stream was mixed with a $NH_4OH$ solution (28–30% by wt $NH_3$) in a ratio of 100 parts of the colored DTDDDS stream to 1 to 2 parts of the $NH_4OH$ solution by weight in a tank at 85° F. to 120° F. to produce a mixture. Since $NH_4OH$ does not readily dissolve in DTDDDS, the mixture was mixed and rolled in the tank for about 15 hours to about 24 hours depending on the color reduction. Plant production yielded acceptable product after about 24 hours of mixing and tank rolling at 120° F. The mixture was then treated with multiple water washings at a temperature range of 70° F. to 100° F. to remove $NH_4OH$ to produce a washed mixture. The washed mixture was allowed to separate in the tank to produce a wet DTDDDS product and a byproduct stream. The wet DTDDDS was dried to produce a DTDDDS product with a color range of about 1 to about 2 on the Gardner color test and a moisture content of less than 10 ppm water by weight.

That which is claimed is:

1. A process to remove color byproducts and residues from a colored DTDDDS stream to produce a ditertiary-dodecyl disulfide (DTDDDS) product, said process comprising;
   (a) Contacting $NH_4OH$ and said colored DTDDDS stream to produce a mixture;
   (b) Water washing said mixture to produce a washed mixture;
   (c) Separating said washed mixture to produce a byproduct stream and a wet DTDDDS product,
   (d) Drying said wet DTDDDS product to produce said DTDDDS product.

2. A process according to claim 1 wherein said $NH_4OH$ is a $NH_4OH$ solution containing about 25% to about 35% $NH_3$ by weight.
3. A process according to claim 2 wherein said $NH_4OH$ solution contains about 28% to about 32% $NH_3$ by weight.
4. A process according to claim 1 wherein said contacting occurs at a temperature range of about 85° F. to about 120° F.
5. A process according to claim 4 wherein said contacting occurs during a time of about 24 hours to about 48 hours.
6. A process according to claim 1 wherein said water washing occurs in a temperature range of about 80° F. to about 90° F.
7. A process according to claim 1 wherein said separating occurs in a temperature range of about 70° F. to about 100° F.
8. A process according to claim 5 wherein said separating occurs during a duration of about 48 hours to about 72 hours.
9. A process according to claim 1 wherein said drying occurs for a sufficient duration to produce a DTDDDS product having less than about 10 ppm, water by weight.
10. A process to remove color byproducts and residues from a colored DTDDDS stream to produce a ditertiary-dodecyl disulfide (DTDDDS) product, said process comprising:
    (a) Contacting a 28% to 30% by weight $NH_4OH$ solution with said colored DTDDDS stream to produce a mixture, wherein said contacting is conducted at a temperature in the range of about 85° F. to about 120° F. and for a duration in a range of about 24 to about 48 hours wherein said $NH_4OH$ solution is contacted with said colored DTDDDS stream in a concentration ratio of 1 to 2 parts $NH_4OH$ solution to 100 parts of said colored DTDDDS stream;
    (b) water washing said mixture with a quantity of water ranging from about 10% to about 30% by weight of said colored DTDDDS stream at a temperature range of about 70° F. to 100° F. to produce a washed mixture;
    (c) separating said washed mixture at a temperature range of about 70° F. to 100° F. and is a duration of about 2 hours to about 72 hours to produce a byproduct stream and a wet DTDDDS stream; and
    (d) drying said wet DTDDDS stream at a temperature range of about 70° F. to about 100° F. to produce a DTDDDS product; wherein said DTDDDS product has a color range of about 1 to about 2 on a Gardner color test and a moisture content of less than about 100 ppm by weight water.

* * * * *